US006254726B1

(12) United States Patent
Steiner et al.

(10) Patent No.: US 6,254,726 B1
(45) Date of Patent: Jul. 3, 2001

(54) PROCESS AND APPARATUS FOR DETECTING MOISTURE CONTENT IN A SUPPORTED FIBROUS WEB

(75) Inventors: Karl Steiner, Herbrechringen; Thomas Augscheller, Bachhagel; Frank Wegehaupt, Böhmenkirch, all of (DE)

(73) Assignee: Voith Sulzer Papiertechnik Patent GmbH, Heidenheim (DE)

( * ) Notice: Subject to any disclaimer, the term of this patent is extended or adjusted under 35 U.S.C. 154(b) by 0 days.

(21) Appl. No.: 09/407,987

(22) Filed: Sep. 29, 1999

(30) Foreign Application Priority Data

Sep. 30, 1998 (DE) ........................................ 198 44 927

(51) Int. Cl.[7] ........................ D21F 7/06; G01N 33/34

(52) U.S. Cl. ........................ 162/198; 162/50; 162/263; 162/DIG. 6; 250/339; 250/341

(58) Field of Search ........................ 162/198, 263, 162/50, DIG. 6; 250/339, 341, 358, 360

(56) References Cited

U.S. PATENT DOCUMENTS 4,840,706 * 6/1989 Campbell ........................ 162/198
5,539,634 7/1996 He ........................ 364/158
5,625,962 5/1997 Fleissner ........................ 34/446

FOREIGN PATENT DOCUMENTS 2140757 2/1972 (DE) .
2318032 10/1973 (DE) .
4133439 4/1992 (DE) .
4325915 2/1995 (DE) .
681183 11/1995 (EP) .

* cited by examiner

*Primary Examiner*—Dean T. Nguyen
(74) *Attorney, Agent, or Firm*—Greenblum & Bernstein, P.L.C.

(57) ABSTRACT

Apparatus and process in a machine for at least one of producing and processing the fibrous web. The apparatus includes an essentially water-free traveling surface adapted to guide the fibrous web, and a measuring device positioned and adapted to detect moisture content of the fibrous web while the fibrous web is supported by the essentially water-free traveling surface. The process includes guiding the fibrous web on the essentially water-free traveling surface, and detecting a moisture content of the fibrous web while the fibrous web is supported by the essentially water-free traveling surface.

45 Claims, 2 Drawing Sheets

PROCESS AND APPARATUS FOR DETECTING MOISTURE CONTENT IN A SUPPORTED FIBROUS WEB

CROSS-REFERENCE TO RELATED APPLICATIONS

The present application claims priority under 35 U.S.C. § 119 of German Patent Application No. 198 44 927.5, filed on Sep. 30, 1998, the disclosure of which is expressly incorporated by reference herein in its entirety.

BACKGROUND OF THE INVENTION

1. Field of the Invention

The present invention relates to a measuring system for determining the moisture content of a fibrous web, e.g., a paper or textile web, in a machine for producing and/or processing the fibrous web. The moisture content is determined in a region of the machine in which the fibrous web runs without a free draw, i.e., is supported.

2. Discussion of Background Information

Prior art measuring systems allow the measurement of the moisture content generally only in long, free draws of the fibrous web (i.e., where the web is unsupported). However, due to increasing production speeds, guiding the fibrous web in as closed, i.e., supported, a manner as possible is becoming increasingly important.

A process is known, e.g., from German Patent Application DE-OS 43 25 915, in which the fibrous web is permeated with air. The moisture content of the fibrous web is determined by comparing the incoming air and the outgoing air. However, this determination is too imprecise, particularly when used in connection with high web speeds. Moreover, this determination cannot be made in areas without free draw.

SUMMARY OF THE INVENTION

Therefore, the present invention provides a measuring system that allows moisture content of the fibrous web to be measured even without free draw.

In this regard, the measurement can occur in an area in which the fibrous web rests on an essentially water-free, traveling surface.

The water-free surface guarantees as little distortion as possible of the measurement result. Here, the measurement can be made based upon certain types of radiation such that a degree of absorption of the radiation by the water in the material web can be measured as an indicator of the moisture content of the fibrous web. The source and detector of the radiation can be arranged either on different sides or on the same side of the fibrous web.

In an exemplary embodiment, an intensity of radiation passing through the fibrous web and at least the water-free surface can be measured. In an alternative embodiment, the intensity of reflected radiation can be measured.

Infrared radiators with one or more wavelengths and/or ionizing radiation may be particularly suitable for such measuring.

The essentially water-free surface can be formed by a rotating roll, e.g., a smooth one. Moreover, the rotating roll can be formed by, e.g., a drying cylinder, a press roll, a measuring roll, or a guide roll.

The source and/or detector of radiation can be arranged, e.g., in the interior of the roll and can be positionally fixed, at least in the circumferential direction. When using infrared radiators, it may be particularly advantageous for accuracy of measurement if the roll jacket is formed in an optically transparent manner, at least at one point of the circumferential surface, that is guided past the source and detector.

The construction of the apparatus can be simplified if the roll, e.g., formed as a guide roll, includes an optically transparent roll jacket made of, e.g., plastic.

However, it is also possible to house the source of radiation and/or detector of radiation within the roll jacket. In this case, the source and/or detector of radiation should have an optically transparent covering that does not extend beyond the jacket surface of the roll.

Instead of a roll, a traveling belt, e.g., a smooth belt, in the form of a transfer belt or a press belt can be used to form the water-free surface. The surface of the belt or the roll can also be formed, e.g., with a grooved or blind-bored profile. Suction rolls with perforated roll jackets can also be utilized. Further, the possibility exists to form the essentially water-free surface as a relatively intensively dried wire or felt belt. Advantageously, the measurement of the moisture content of the fibrous web can occur at an end and/or after the press section and/or in the drying section. Moreover, the measurement can occur at a position between first and second drying groups, and/or in a region of a calender.

To measure the moisture cross-direction profile of the fibrous web, the source and/or the detector of the radiation can be arranged to traverse the web in a cross-wise direction. It is also possible to provide several sources and/or detectors perpendicular to a fibrous web run direction.

Therefore, the present invention is directed to an apparatus in a machine for at least one of producing and processing the fibrous web. The apparatus includes an essentially water-free traveling surface adapted to guide the fibrous web, and a measuring device positioned and adapted to detect moisture content of the fibrous web while the fibrous web is supported by the essentially water-free traveling surface.

According to another feature of the invention, the measurement device can operate with infrared radiation having at least one wavelength. The detection of moisture content can be based upon a measurement of a degree of absorption of the radiation by water in the fibrous web. The measuring device can include at least one source and at least one detector adapted to respectively transmit and receive the radiation, and the at least one source and at least one detector can be arranged on different sides of the fibrous web. Alternatively, the at least one source and at least one detector can be arranged on a same side of the fibrous web. Further, the at least one source and the at least one detector may include at least one of a silicon semiconductor or lead sulfide.

In accordance with still another feature of the present invention, the measurement device can operate with ionizing radiation. Further, the ionizing radiation may include one of beta- and delta-radiation.

In accordance with a further feature of the instant invention, the essentially water-free traveling surface is formed as a rotating roll. Further, the rotating roll can be a smooth roll, and the rotating roll may be one of a drying cylinder, a press roll, and a guide roll. Further, the measuring device may include at least one source and at least one detector adapted to respectively transmit and receive the radiation, and the at least one source and the at least one detector can be located in an interior of the roll and positionally fixed in a circumferential direction. Further still, the roll can include a roll jacket having at least optically transparent points on a circumferential surface of the roll jacket. The at least optically transparent points may be positioned to at least axially correspond to the fixed position of the at least one source and at least one detector. Moreover, the roll jacket can be composed entirely of an optically transparent material.

According to another feature of the instant invention, the roll can include a roll jacket, and the at least one source and the at least one detector may be located in the roll jacket. Further, the at least one source and the at least one detector can include an optically transparent covering which does not extend beyond an outer surface of the roll jacket.

According to a still further feature of the present invention, the essentially water-free traveling surface may include a traveling belt. The traveling belt may be a smooth belt, and can be one of a transfer belt and a press belt.

In accordance with still another feature of the invention, the essentially waterfree traveling surface can include a dried one of a traveling wire and felt belt.

According to another feature of the present invention, the measurement device can be located in at least one of at the end of a press section, after the press section, in a drying section, and in a region of a calender. Further, the measurement device can be located between a first and a second drying group.

According to a further feature of the instant invention, the measuring device can include at least one source and at least one detector adapted to respectively transmit and receive a signal. The at least one source and the at least one detector may be arranged to traverse the fibrous web in a cross-wise direction.

In accordance with still another feature of the present invention, a plurality of sources and a plurality of detectors can be arranged next to one another in a direction cross-wise to the fibrous web.

According to yet another feature of the invention, the fibrous material may be one of a paper and a textile web.

The present invention is also directed to a process for use with an apparatus in a machine for one of producing and processing a fibrous web. The apparatus can include an essentially water-free traveling surface and a measuring device, and the process includes guiding the fibrous web on the essentially water-free traveling surface, and detecting a moisture content of the fibrous web while the fibrous web is supported by the essentially water-free traveling surface.

According to another feature of the present invention, the detecting of moisture content may include transmitting a signal toward a portion of the fibrous web that is supported by the essentially water-free traveling surface, receiving a portion of the signal reflected from the portion of the fibrous web that is supported by the essentially water-free traveling surface, and determining moisture content based upon a degree of absorption of the signal by the water in the fibrous web. The signal can include one of infrared radiation and ionizing radiation. The infrared radiation may include at least one wavelength of approximately 1.9 μm and the ionizing radiation may include one of β- and δ-radiation.

In accordance with still another feature of the invention, the detecting of moisture content can include transmitting a signal toward a portion of the fibrous web that is supported by the essentially water-free traveling surface, receiving a portion of the signal passing through the portion of the fibrous web that is supported by the essentially water-free traveling surface, and determining moisture content based upon a degree of absorption of the signal by the water in the fibrous web. The signal can include one of infrared radiation and ionizing radiation. The infrared radiation may include at least one wavelength of approximately 1.9 μm and the ionizing radiation may include one of β- and δ-radiation.

In accordance with a further feature of the invention, the apparatus may further include at least one source of a signal and at least one detector of the signal which are located within a roll formed by the essentially water-free traveling surface, and the process can include transmitting the signal through an optically transparent portion of the roll that is supporting the fibrous web, receiving a portion of the signal reflected from the fibrous web, and determining moisture content based upon a degree of absorption of the signal by the water in the fibrous web. The signal can include one of infrared radiation and ionizing radiation. The infrared radiation may include at least one wavelength of approximately 1.9 μm and the ionizing radiation may include one of β- and δ-radiation.

In accordance with a still further feature of the instant invention, the apparatus may further include at least one source of a signal and at least one detector of the signal which are located within the essentially water-free traveling surface, and the essentially water-free traveling surface can be formed as a roll, and the process can further include transmitting the signal through an optically transparent covering of the at least one sensor of the roll, which is mounted flush with an outer surface of the roll and which is supporting the fibrous web, receiving a portion of the signal reflected from the fibrous web, and determining moisture content based upon a degree of absorption of the signal by the water in the fibrous web. The signal can include one of infrared radiation and ionizing radiation. The infrared radiation may include at least one wavelength of approximately 1.9 μm and the ionizing radiation may include one of β- and δ-radiation.

According to yet another feature of the present invention, the apparatus may further include one of at least one source of a signal and at least one detector of the signal being located within a roll formed by the essentially water-free traveling surface and the other of the one of at least one source of radiation and at least one detector of radiation being located outside of the roll, and the process can further include transmitting the signal toward a portion of the fibrous web supported by the roll, receiving a portion of the signal passing through the portion of the fibrous web, and determining moisture content based upon a degree of absorption of the radiation by the water in the fibrous web. The signal can include one of infrared radiation and ionizing radiation. The infrared radiation may include at least one wavelength of approximately 1.9 μm and the ionizing radiation may include one of β- and δradiation.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

In the figures, the measurement of moisture content of the fibrous web 1 can occur in a region of a machine for producing fibrous web 1, which can run without a free draw, i.e., supported, so that fibrous web 1 rests on an essentially water-free, traveling surface. In this regard, the essentially water-free traveling surface can be made of, e.g., ceramics, polyamid, rubber, polyurethane, steel.

Measurement can be made with, e.g., infrared radiation having one or more wavelengths or weak ionizing radiation. A degree of absorption of the radiation by the water in fibrous web 1 can be measured as an indicator of moisture content. The infrared radiation can include, e.g., a wavelength of approximately 1.9 $\mu$m or a combination of different wavelengths, and the ionizing radiation can include, e.g., $\delta$-radiation and $\beta$-radiation.

Figure 1:
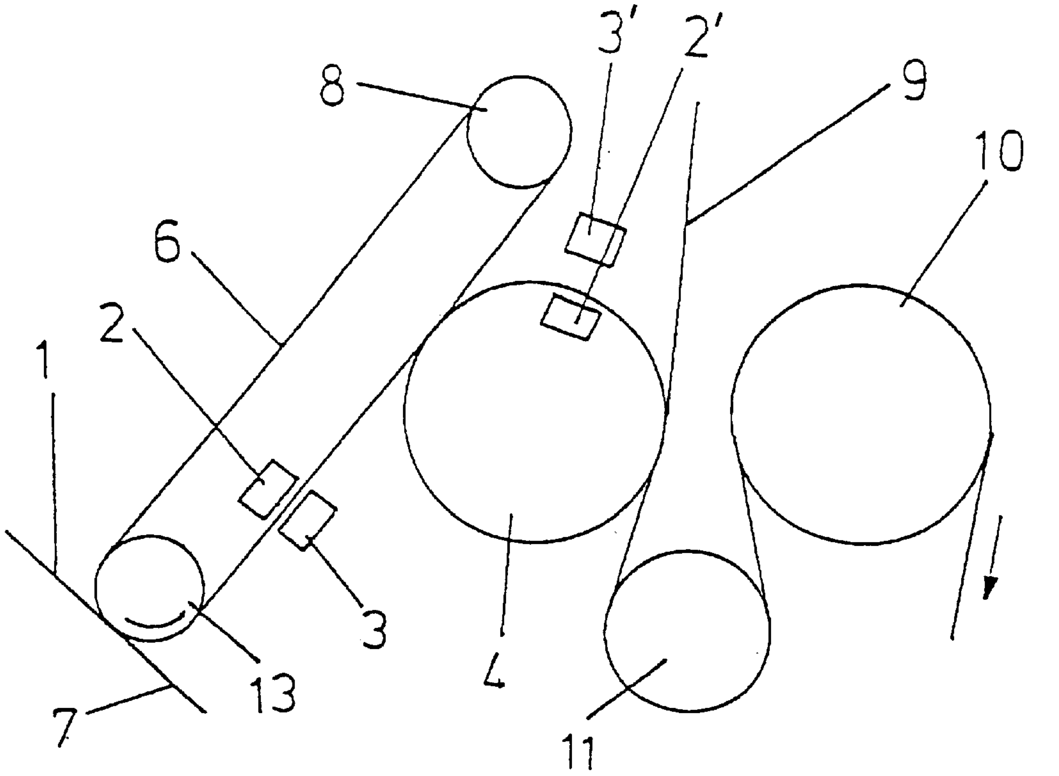
FIG. 1 schematically illustrates a measurement position after a press section and at a beginning of a drying group.

In FIG. 1, fibrous web 1 is transferred onto an endless wire belt 6 from a felt belt 7 via a suction guide roll 13 of wire belt 6. Subsequently, measurement of moisture content can be made with a source (transmitter) 2, e.g., of infrared radiation composed of, e.g., a silicon semiconductor or lead sulfide, and a detector (receiver) 3, e.g., of infrared radiation composed of, e.g., a silicon semiconductor or lead sulfide. As shown in the exemplary embodiment, source 2 and detector 3 may be arranged on different sides of fibrous web 1 and/or wire belt 6. As a result, the amount of radiation penetrating fibrous web 1 and wire belt 6 can be measured. To guarantee as dry a surface as possible, wire belt 6 should be preferably dried, e.g., via heated guide rolls 8.

Fibrous web 1 can subsequently be transferred to an unheated and rotating roll 4, e.g., a smooth roll, within a subsequent drying group. The surface of roll 4 can be an essentially water-free surface, and can be utilized for measuring moisture content of fibrous web 1. At this position, measurement can be made via source 2', e.g., of weak ionizing radiation, which may be located within an interior of roll 4. Detector 3, e.g., of weak ionizing radiation, can be located outside of roll 4 and positioned opposite source 2. Roll 4 can subsequently transfer fibrous web 1 onto a drying wire 9, which guides fibrous web 1 alternately over guide rolls 11 and heated drying cylinders 10 of the drying group.

Further, it is noted that, in accordance with the present invention, the determination of moisture content can be made from empirically derived moisture content data that is, e.g., stored in an appropriate storage device such as a computer memory. Thus, for specified infrared or weak ionizing radiation transmitted and received, the moisture content can be easily obtained.

Figure 2:
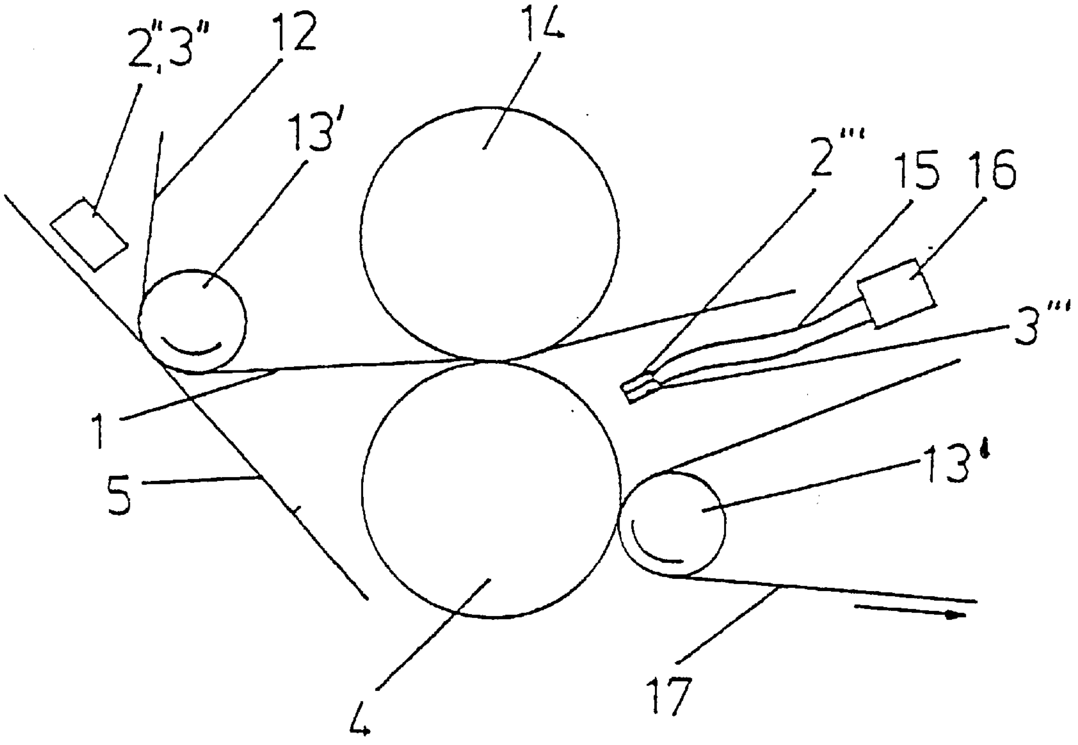
FIG. 2 schematically illustrates the measurement position at an end of the press section.

In contrast to the exemplary embodiment, FIG. 2 schematically illustrates source 2" and detector 3" of radiation, which can be located on a same side of fibrous web 1. Consequently, an amount of reflected radiation can be measured.

Fibrous web 1 can be transferred from a traveling (transfer) belt 5, e.g., a smooth belt, onto a press felt 12 that is supported by a suctioned guide roll 13'. Because belt 5 can be formed with an essentially water-free surface, measurement of moisture content can occur before the transfer to press belt 12, with source 2, e.g., of infrared radiation, and detector 3, e.g., of infrared radiation, arranged on the free side of fibrous web 1.

Together with endless pressing felt 12, fibrous web 1 can be guided through a press nip or gap formed by rolls 4' and 14, so that water can be pressed out and can be absorbed and removed by press felt 12. After the press nip, fibrous web 1 can be separated from press felt 12 and guided along roll 4', e.g., a smooth roll, until being transferred to a transfer wire 17 via a suction guide roll 13'.

Because roll 4' is formed of a material to provide an essentially water-free surface, measurement of moisture content of fibrous web 1 can occurs between the press nip and the transfer to transfer wire 17. Here, source 2, e.g., of infrared radiation, and detector 3, e.g., of infrared radiation, can be arranged in a winding area of roll 4', i.e., an area in which fibrous web 1 is guided over and supported by roll 4', and can be connected through a light guide 15 to an evaluation unit 16. Such an arrangement can simplify the access to the measuring points.

Measurement on wire belt 6 (FIG. 1) and on belt 5 (FIG. 2) can be made, e.g., by a traversing of a source 2 or 2" and detector 3 or 3" cross-wise to a belt travel direction. In a further example, source 2' can be located inside roll 4 and several detectors 3' can be located outside of and arranged along the length of the roll 4. Further, several sources 2" and detectors 3" can be arranged along the length of roll 4'. However, these arrangements are only exemplary and it is contemplated that each arrangement can be suited for use in the variously disclosed locations of the web production machine.

As shown in FIG. 1, the measurement system can be arranged, e.g., between the drying groups. In general, the measurement described herein can occur within a range of, e.g., between approximately 30 and 75% absolute dry, and preferably between approximately 30 and 65% absolute dry.

Figure 3:
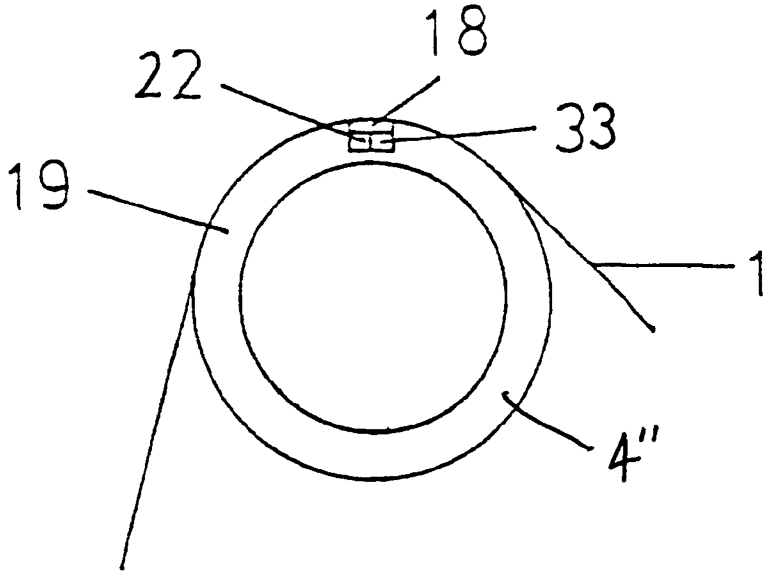
FIG. 3 schematically illustrates the measurement position in which the source and the detector are located within a surface of a roll jacket.

FIG. 3 schematically illustrates a cross-section of a roll 4", in which at least one infrared source 22 and at least one infrared detector 33 can be positioned next to each other in a circumferential direction, and, e.g., a plurality of the circumferentially arranged infrared source(s) 22 and detector(s) 33 can be axially arranged next to one another. The infrared source(s) 22 and detector(s) 33 can be disposed in the surface of roll jacket 19 of roll 4". Source(s) 22 and the detector(s) 33 can be protected by an optically transparent covering 18, which ends at the jacket surface of roll 4". Source(s) 22 and detector(s) 33, which, as noted above, can be arranged next to each other, can provide adequate measurement of the moisture content of fibrous web 1, and with a high speed of rotation of roll jacket 19, a high frequency of measurement can result. Thus, rotation of the source(s) 22 and detector(s) 33 do not cause any measurement problems. As a result, an evaluation is possible only when a source 22 and a detector 33 are located in a region in which fibrous web 1 is supported by roll jacket 19.

This arrangement, in addition to shielding of the measurement system from outside influences, also provides savings in space and a defined, short measuring distance between source 22 (and detector 33) and fibrous web 1.

Figure 4:
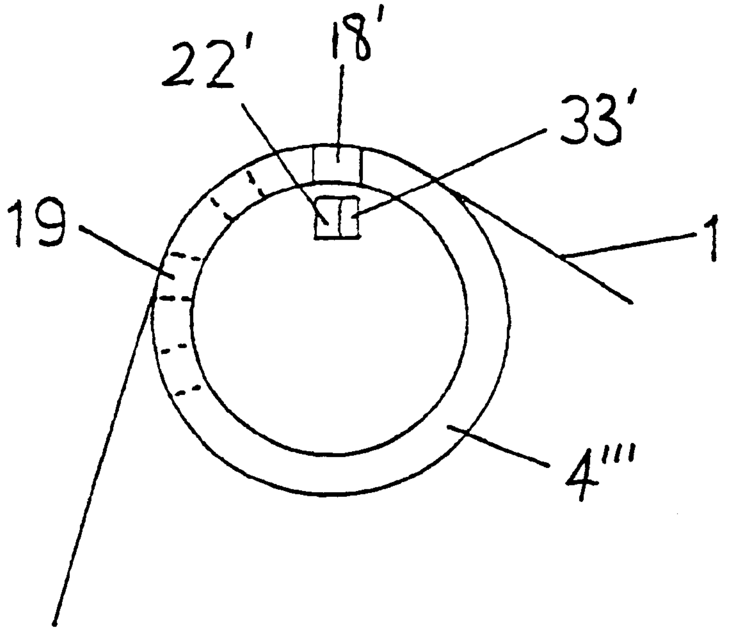
FIG. 4 schematically illustrates the measurement position in which the source and the detector are located within an interior of the roll jacket.

In contrast, FIG. 4 illustrates that at least one source 22' and at least one detector 33' can be positioned next to each other in a circumferential direction and fixedly positioned in the axial and circumferential direction in the interior of roll 4''', i.e., within roll jacket 19'. Moreover, a plurality of the source(s) 22' and detector(s) 33' can be axially arranged within roll jacket 19'. Roll jacket 19' can be formed of an optically transparent material, e.g., plastic or polyurethane, at points on its circumferential surface that correspond with the positions of source(s) 22' and detector(s) 33'. Further, these points may be arranged to be offset from one another in order to ensure sufficient stability of roll 4''' in the circumferential direction.

Moreover, maximum shielding of the measurement system can occur in the roll, which can be formed to be a completely optically transparent guide or measuring roll jacket made of, e.g., plastic or polyurethane.

Further, a plurality of axial rows formed by combinations of source(s) 22' and detector(s) 33' can be located within roll 4'''.

While the various exemplary embodiments have been described herein as utilizing particular types of radiation, it is noted that these descriptions are for the purposes of explanation and illustration and are not meant to be construed as limiting in any manner. In this regard, it is noted that the various exemplary embodiments can utilize any of the disclosed types of radiation or other similar transmission signals that would enable a detection of the transmitted signal, either passing through or reflected from the fibrous web in a non-free draw, in which the signal is altered to due to a water content of the fibrous web.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A process for use with an apparatus in a machine for one of producing and processing a fibrous web, the apparatus including an essentially water-free traveling surface and a measuring device, the process comprising:

guiding the fibrous web on the essentially water-free traveling surface; and detecting a moisture content of the fibrous web where the fibrous web is supported by the essentially water-free traveling surface.

2. The process in accordance with claims 1, wherein the detecting of moisture content comprises:

transmitting a signal toward a portion of the fibrous web that is supported by the essentially water-free traveling surface;

receiving a portion of the signal reflected from the portion of the fibrous web that is supported by the essentially water-free traveling surface; and determining moisture content based upon a degree of absorption of the signal by the water in the fibrous web.

3. The process in accordance with claim 2, wherein the signal comprises one of infrared radiation and ionizing radiation.

4. The process in accordance with claim 3, wherein the infrared radiation includes at least one wavelength of approximately 1.9 μm and the ionizing radiation includes one of β- and δ-radiation.

5. The process in accordance with claim 1, wherein the detecting of moisture content comprises:

transmitting a signal toward a portion of the fibrous web that is supported by the essentially water-free traveling surface;

receiving a portion of the signal passing through the portion of the fibrous web that is supported by the essentially water-free traveling surface; and determining moisture content based upon a degree of absorption of the signal by the water in the fibrous web.

6. The process in accordance with claim 5, wherein the signal comprises one of infrared radiation and ionizing radiation.

7. The process in accordance with claim 6, wherein the infrared radiation includes at least one wavelength of approximately 1.9 μm and the ionizing radiation includes one of β- and δ-radiation.

8. The process in accordance with claim 1, wherein the apparatus further includes at least one source of a signal and at least one detector of the signal which are located within a roll formed by the essentially water-free traveling surface, and the process further comprises:

transmitting the signal through an optically transparent portion of the roll that is supporting the fibrous web;

receiving a portion of the signal reflected from the fibrous web; and determining moisture content based upon a degree of absorption of the signal by the water in the fibrous web.

9. The process in accordance with claim 8, wherein the signal comprises one of infrared radiation and ionizing radiation.

10. The process in accordance with claim 9, wherein the infrared radiation includes at least one wavelength of approximately 1.9 μm and the ionizing radiation includes one of β- and δ-radiation.

11. The process in accordance with claim 1, wherein the apparatus further includes at least one source of a signal and at least one detector of the signal which are located within the essentially water-free traveling surface, and the essentially water-free traveling surface is formed as a roll, and the process further comprises:

transmitting the signal through an optically transparent covering of the at least one sensor of the roll, which is mounted flush with an outer surface of the roll and which is supporting the fibrous web;

receiving a portion of the signal reflected from the fibrous web; and determining moisture content based upon a degree of absorption of the signal by the water in the fibrous web.

12. The process in accordance with claim 11, wherein the signal comprises one of infrared radiation and ionizing radiation.

13. The process in accordance with claim 12, wherein the infrared radiation includes at least one wavelength of approximately 1.9 μm and the ionizing radiation includes one of β- and δ-radiation.

14. The process in accordance with claim 1, wherein the apparatus further includes one of at least one source of a signal and at least one detector of the signal located within a roll formed by the essentially water-free traveling surface and the other of the one of at least one source of radiation and at least one detector of radiation located outside of the roll, and the process further comprises:

transmitting the signal toward a portion of the fibrous web supported by the roll;

receiving a portion of the signal passing through the portion of the fibrous web; and determining moisture content based upon a degree of absorption of the radiation by the water in the fibrous web.

15. The process in accordance with claim 14, wherein the signal comprises one of infrared radiation and ionizing radiation.

16. The process in accordance with claim 15, wherein the infrared radiation includes at least one wavelength of approximately 1.9 $\mu$m and the ionizing radiation includes one of β- and δ-radiation.

17. An apparatus in a machine for at least one of producing and processing the fibrous web, comprising:

an essentially water-free traveling surface structured and arranged to guide the fibrous web; and a measuring device structured and arranged to detect moisture content of the fibrous web where the fibrous web is supported by the essentially water-free traveling surface.

18. The apparatus in accordance with claim 17, wherein said measurement device operates with infrared radiation having at least one wavelength.

19. The apparatus in accordance with claim 18, wherein the detection of moisture content is based upon a measurement of a degree of absorption of the radiation by water in the fibrous web.

20. The apparatus in accordance with claim 18, said measuring device comprising at least one source and at least one detector adapted to respectively transmit and receive the radiation; and said at least one source and at least one detector being arranged on different sides of the fibrous web.

21. The apparatus in accordance with claim 18, said measuring device comprising at least one source and at least one detector adapted to respectively transmit and receive the radiation; and said at least one source and at least one detector being arranged on a same side of the fibrous web.

22. The apparatus in accordance with claim 21, said at least one source and said at least one detector comprising at least one of a silicon semiconductor or lead sulfide.

23. The apparatus in accordance with claim 17, wherein said at least one wavelength is approximately 1.9 $\mu$m.

24. The apparatus in accordance with claim 17, wherein said measurement device operates with ionizing radiation.

25. The apparatus in accordance with claim 24, wherein the detection of moisture content is based upon a measurement of a degree of absorption of the radiation by water in the fibrous web.

26. The apparatus in accordance with claim 24, said measuring device comprising at least one source and at least one detector adapted to respectively transmit and receive the radiation; and said at least one source and at least one detector being arranged on different sides of the fibrous web.

27. The apparatus in accordance with claim 24, said measuring device comprising at least one source and at least one detector adapted to respectively transmit and receive the radiation; and said at least one source and at least one detector being arranged on a same side of the fibrous web.

28. The apparatus in accordance with claim 24, said ionizing radiation including one of beta- and delta-radiation.

29. The apparatus in accordance with claim 17, wherein said essentially water-free traveling surface is formed as a rotating roll.

30. The apparatus in accordance with claim 29, wherein the rotating roll is a smooth roll.

31. The apparatus in accordance with claim 29, wherein said rotating roll is one of a drying cylinder, a press roll, and a guide roll.

32. The apparatus in accordance with claim 29, said measuring device comprising at least one source and at least one detector adapted to respectively transmit and receive the radiation; and said at least one source and said at least one detector being located in an interior of said roll and positionally fixed in a circumferential direction.

33. The apparatus in accordance with claim 32, said roll comprising a roll jacket comprising at least optically transparent points on a circumferential surface of said roll jacket;

said at least optically transparent points being positioned to at least axially correspond to the fixed position of said at least one source and at least one detector.

34. The apparatus in accordance with claim 33, said roll jacket being composed entirely of an optically transparent material.

35. The apparatus in accordance with claim 29, said roll comprising a roll jacket; and said at least one source and said at least one detector being located in said roll jacket.

36. The apparatus in accordance with claim 35, said at least one source and said at least one detector comprising an optically transparent covering which does not extend beyond an outer surface of said roll jacket.

37. The apparatus in accordance with claim 17, said essentially water-free traveling surface comprising a traveling belt.

38. The apparatus in accordance with claim 37, said traveling belt having a smooth belt.

39. The apparatus in accordance with claim 37, said traveling belt being one of a transfer belt and a press belt.

40. The apparatus in accordance with claim 17, said essentially water-free traveling surface comprising a dried one of a traveling wire and felt belt.

41. The apparatus in accordance with claim 17, wherein said measurement device is located in at least one of at the end of a press section, after the press section, in a drying section, and in a region of a calender.

42. The apparatus in accordance with claim 41, wherein said measurement device is located between a first and a second drying group.

43. The apparatus in accordance with claim 17, said measuring device comprising at least one source and at least one detector adapted to respectively transmit and receive a signal; and said at least one source and said at least one detector being arranged to traverse the fibrous web in a cross-wise direction.

44. The apparatus in accordance with claim 17, wherein a plurality of sources and a plurality of detectors are arranged next to one another in a direction cross-wise to the fibrous web.

45. The apparatus in accordance with claim 17, wherein the fibrous material comprises one of a paper and a textile web.

* * * * *